United States Patent [19]
Kucherov

[11] Patent Number: 6,019,947
[45] Date of Patent: Feb. 1, 2000

[54] METHOD AND APPARATUS FOR STERILIZATION OF A CONTINUOUS LIQUID FLOW

[75] Inventor: Yan R. Kucherov, Salt Lake City, Utah

[73] Assignee: Cavitech, Inc., Salt Lake City, Utah

[21] Appl. No.: 09/102,614

[22] Filed: Jun. 22, 1998

[51] Int. Cl.[7] .................................. B06B 1/20; A61L 2/02
[52] U.S. Cl. .............................. 422/128; 422/20; 422/93; 210/748
[58] Field of Search ............................... 422/20, 128, 39; 210/748

[56] References Cited

U.S. PATENT DOCUMENTS

| | | | |
|---|---|---|---|
| 2,693,944 | 11/1954 | Fowle | 422/20 X |
| 4,003,832 | 1/1977 | Henderson et al. | 210/19 |
| 4,961,860 | 10/1990 | Masri | 422/20 X |
| 5,383,944 | 1/1995 | Matsui | 422/128 X |
| 5,395,592 | 3/1995 | Bolleman et al. | 422/128 |
| 5,466,425 | 11/1995 | Adams | 422/186.3 |
| 5,494,585 | 2/1996 | Cox | 210/748 |
| 5,519,670 | 5/1996 | Walter | 367/142 |
| 5,611,993 | 3/1997 | Babaev | 422/20 |

OTHER PUBLICATIONS

Burleson, Gary R., "Inactivation of Viruses and Bacteria by Ozone, With and Without Sonication", *Applied Microbiology*, vol. 29, No. 3 (Mar. 1975), pp. 340–344.

Doulah, M.S., "Mechanism of Disintegration of Biological Cells in Ultrasonic Cavitation", *Biotechnology and Bioengineering*, vol. XIX, (1977), pp. 649–660.

Sanada, N. et al., "Interaction of a Gas Bubble with an Underwater Shock Wave, Pit Formation on the Metal Surface", *Shock Tubes & Waves:* Proceedings of the Sixteenth International Symposium on Shock Tubes and Waves, (Jul. 26–31, 1987) pp. 312–317.

Kitayama, O. et al., "Non–Invasive Gallstone Disintegration by Underwater Shock Focusing", *Shock Tubes & Waves:* Proceedings of the Sixteenth International Symposium on Shock Tubes and Waves, (Jul. 26–31, 1987) pp. 897–903.

Suslick, Kenneth S., "Ultrasound Its Chemical, Physical, and Biological Effects", *Ultrasound*, (1988), pp. 108, 120–121.

*Primary Examiner*—E. Leigh McKane
*Attorney, Agent, or Firm*—Paul S. Evans

[57] ABSTRACT

The apparatus for liquid sterilization by high-pressure dynamic cavitation includes a fluid passage through which the continuous flow of liquid passes, wherein the fluid passage is defined by a closed cylindrical chamber having a side wall and first and second opposing ends. The chamber has an inlet and an outlet through which the continuous flow of liquid enters and exits the chamber, the inlet being tangential to the chamber axis and adjacent to the first end to provide tangential flow within the chamber and to cause the liquid flow to be deflected at the first and second opposing ends two or more times for increasing sterilization time of the liquid before exiting the outlet axially disposed on the second end. One or more projections protruding from the interior side wall of the chamber create a high-pressure drop in the flow behind the one or more projections and thereby create high-pressure dynamic cavitation for effective sterilization.

16 Claims, 6 Drawing Sheets

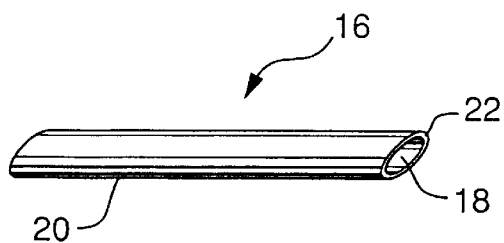
FIG. 3
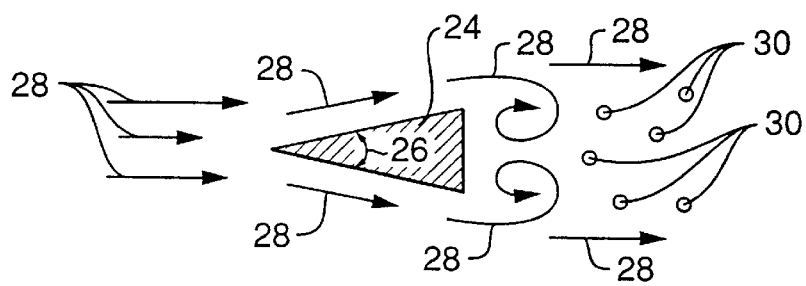
FIG. 4
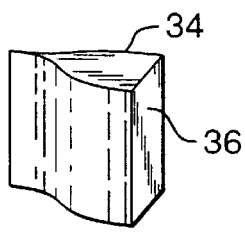 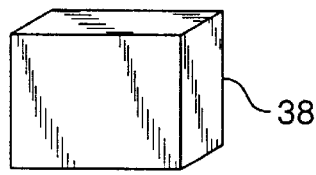 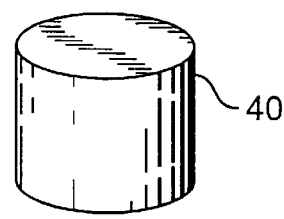
FIG. 5   FIG. 6   FIG. 7
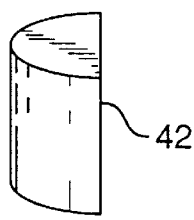 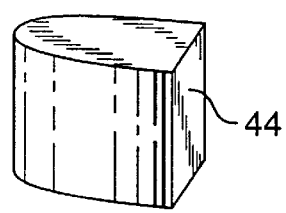
FIG. 8   FIG. 9

METHOD AND APPARATUS FOR STERILIZATION OF A CONTINUOUS LIQUID FLOW

FIELD OF THE INVENTION

This invention relates to methods and apparatus for sterilization of a continuous flow of liquid, and more particularly to such methods and apparatus which utilize hydrodynamic cavitation.

BACKGROUND OF THE INVENTION

The present invention was developed to fill a need for a method and apparatus which will sterilize and purify a liquid flow, particularly from bacteria, without the use of chemical additives.

Attempts have been made to alleviate this problem by utilizing cavitation. However, the methods and apparatus currently available require an extended exposure time of the liquid before a sufficient amount of bacteria is eliminated. This extended exposure time in many instances renders the process uneconomical.

From a mechanical point of view, most bacteria can be characterized as liquid droplets with an envelope of typically 1–10 microns in size (Paul Singleton, Bacteria in Biology, Biotechnology and Medicine, Wiley, 1993). In most bacteria, a tough outer layer (the cell wall) protects the inner protoplast from mechanical damage and osmotic lysis. Two major types of cell walls exist. The type of a cell wall can be determined by the cell's reaction to certain dyes. Cells of a Gram-positive type retain specific dyes. Cells of a Gram-negative type do not retain dye and become decolorized.

Cell walls of Gram-positive bacteria are relatively thick, having a thickness of about 30–100 nanometers. Some 40–80% of the cell wall is made of a tough, complex polymer named peptidoglycan. Peptidoglycan may consist of linear heteropolysacharide chains that are cross-linked by short peptides. Cell walls of Gram-negative type bacteria are thinner, having a thickness of about 20–30 nanometers, which are easier to destroy. The actual mechanical properties of peptidoglican are not known, but evidently it is weaker than polyethelene ($\sigma$=15 MPa or 1.5 Kg/mm$^2$). A more detailed layout of peptidoglycan in bacterial membranes is set forth in Leive, L. *Bacterial Membranes and Walls*. N.Y., Marcel Dekker, 1973. pp. 85–103.

Disinfection by static cavitation is disclosed in U.S. Pat. No. 4,003,832, issued Jan. 18, 1977 to Henderson et al. for Method of Applying Ozone and Sonic Energy to Sterilize and Oxidize Waste Water.

There are several major effects associated with cavitation that can effect bacteria, including: shock waves, micro-liquid jets, ultraviolet due to sonoluminescence, acceleration/deceleration, and the temperature in the gas bubble. Many of these cavitation related effects are disclosed in Young, F. R. *Cavitation*. London, McGraw-Hill Book Co., 1989, the contents of which are incorporated herein by reference.

Temperature in the Gas Bubble

U.S. Pat. No. 5,494,585, issued Feb. 27, 1996 to Dale W. Cox for Water Remediation and Purification System and Method, discloses a cavitation nozzle for creating high localized pressures and temperatures which cause chemical dissociation in the organic contaminants. Indeed, high temperatures exist during the collapse of cavitation bubble, with localized temperatures in excess of 1000° C. (see Young. R. *Cavitation*. supra). However, the net effect on the total volume of water to be treated is small, otherwise, the average water temperature must approach the same values.

Acceleration/Deceleration Effects

For evaluation of the effects of acceleration/deceleration on bacteria, assume that a bacteria cell is a sphere 2 microns in diameter, with 20 nm wall thickness made of entirely peptidoglican and filled with water. At a water flow turning point where the water deflects off of the ends of a cylindrical chamber, the flow sees a boundary layer of approximately 1 mm in thickness. A flow speed of 20 m/s with a 90° turn in the flow corresponds to an acceleration of a~10$^6$ m/s$^2$. The force F, corresponding to this acceleration, must be compensated by the bacterial carcass. It is possible to estimate values for F=ma, where the bacteria mass m equals $\rho$(4/3) $\pi r^3$, where $\rho$ is the water density and r is the radius of the bacteria. In our case, m=4·10$^{-15}$ Kg. The bacteria wall cross-sectional area is S=2$\pi$rt, where t is the wall thickness. From here, the stress on the wall follows the equation $\sigma$=F/S≈0.3 MPa. This stress does not guarantee the destruction of the bacterial wall.

U.V. Due to Sonoluminescence

The effects of ultraviolet are difficult to estimate, since sonoluminescence effects depend on a variety of factors, such as pressure, dissolved gases, temperature, etc. Utilizing FIG. 5.17 from Young. R. *Cavitation*, supra, at p.343 for Ar, which is the most abundant inert gas in the air, and assuming 10$^5$–10$^6$ collapses of cavitational bubbles per second, provides an argon gas ultraviolet source having an intensity of approximately 10$^{-2}$ watt. This intensity is distributed through the water volume more efficiently than the radiation from a typical sterilization UV lamp.

Preferred geometries can improve the effect by 2–3 orders of magnitude and may allow sonoluminescence effects to be comparable with that of a standard UV lamp. Since the sterilization time for UV lamps is measured in hours, which is about 100 times longer than that caused by cavitation, the sterilization related to sonoluminescence is probably a secondary effect.

Micro-liquid Jets

Micro-liquid jets associated with the collapse of cavitational bubbles have a water velocity of at least 200–300 m/s. The boundary layer in this case is extremely small (less than 0.1 mm). Only a limited class of materials can withstand such a violent phenomenon, and certainly not a bacterial wall. Micro-liquid jets evidently kill bacteria. However, since the liquid volume effected by micro-jets is so small, the exposition (exposure) time requires hours for optimized conditions.

Shock Waves

One of the profound effects of cavitation is the generation of shock waves. During the collapse of the cavitation bubble, the cavity wall moves at a speed comparable to the speed of sound in the liquid (1485 m/s in water at 20° C.). It is believed that the shock wave forms on the rebound of the implosion. The shock wave propagation speed depends on the maximum pressure developed in the collapsing bubble. The over-pressure in the bubble can reach 2.3 kilobars, which corresponds to a shock wave propagation speed of around 8000 m/s (see Walsh J. M., Rice M. H. *J Chem. Phys.* 1957, Vol. 26, pp. 815–819). Direct measurements of the thickness of a shock wave front in water give values of 20–50 microns (N. Sanada et. al, in: *Shock Tubes and Waves*, edited by Hans Gronig, Rheinisch-Westofalische Technische Mochschule, Aachen, 1987, p.317). The effect on bacteria is illustrated in FIG. 1, where the bacteria cell wall 3 is stressed by tearing forces 8 created by the propagation 6 of the shock wave front 4 on a bacterial cell 2. With a "modest" maximum pressure of 100 bar on the bacteria model described previously, the stress on the bacterial wall will be 20 MPa, and at maximum pressure of 1 kilobar the stress on the bacteria wall may be 200 MPa. These stresses are sufficient to destroy any bacterial walls.

The shock will remain strong only within a few radial distances from the bubble, due to attenuation. The accepted distance is 5–6 bubble radii.

Pressure Dependence of Cavitation Shock Wave Formation

The maximum pressure generated during the collapse of cavitation bubble is normalized to the ambient pressure. For example, at 30 atmospheres it is 30 times higher than at 1 atmosphere. More important is the fact that the collapsing bubble wall velocity is a non-linear function of the ratio of the maximum pressure to the minimum pressure $P_m/Q$. The minimum pressure Q, in most cases, equals the vapor pressure of the liquid (for water, Q=0.023 atm. at 20° C.). The majority of the bubbles go from this pressure to ambient, giving a $P_m/Q$ ratio of 43 for 1 atmosphere. This corresponds to a wall velocity below 0.1 C, where C is the speed of sound. For pressures higher than 4 atmospheres, $P_m/Q$ is always more than 120, which results in a supersonic wall velocity and guarantees the formation of a shock wave. At 1 atmosphere static pressure, a shock wave formation is the exception, rather than the rule. In other words, 4–5 atmospheres is a practical low operation pressure limit for any shock wave, cavitation-based sterilization device. Very high pressures are also not practical, since it is difficult to create cavitation bubbles. The upper practical pressure limit is certainly below 100 atmospheres.

There remains a need to provide a more satisfactory solution to sterilizing and purifying liquid.

SUMMARY OF THE INVENTION

The present invention seeks to resolve a number of the problems which have been experienced in the background art, as identified above. More specifically, the apparatus and method of this invention constitute an important advancement in the art of liquid sterilization, as evidenced by the following objects and advantages realized by the invention over the background art.

One object of the present invention is to utilize high pressure dynamic cavitation to kill bacteria, utilizing high volume liquid flows.

A further object of the present invention is to develop a high pressure cavitation zone.

Additionally, it is an object of the present invention to subject bacteria to a developed cavitation zone at a high pressure for a sufficient period of time to provide for a high volume, high bacteria kill ratio.

Yet another object of the present invention is to subject the entire liquid flow to a developed cavitation zone, to ensure the absence of untreated pockets.

A further object of the present invention is to provide a bacteria treatment time that is significantly shorter than in known ultrasound methods.

Another object of the present invention is to eliminate the use of chemicals for sterilization purposes.

Additional objects and advantages of the invention will be apparent from the description which follows, or may be learned by the practice of the invention.

Briefly summarized, the foregoing objects are achieved by an apparatus which comprises a fluid passage through which the continuous flow of liquid passes, wherein the fluid passage is defined by a closed cylindrical chamber having a side wall and first and second opposing ends. The chamber has an inlet and an outlet through which the continuous flow of liquid enters and exits the chamber, the inlet being tangential to the chamber axis and adjacent to the first end to provide tangential flow within the chamber and to cause the liquid flow to be deflected at the first and second opposing ends two or more times for increasing sterilization time of the liquid before exiting the outlet disposed on the second end. One or more projections protruding from the side wall of the chamber create high-pressure drop in the flow behind the one or more projections and thereby create high-pressure dynamic cavitation with guaranteed shock wave formation.

BRIEF DESCRIPTION OF DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which:

FIG. 3 is a side view of an inlet nozzle of the present invention.

FIG. 4 is a top view of a wedge-shaped projection in the path of a liquid flow for creating hydrodynamic cavitation.

FIG. 5 is a perspective view of a laminar flow body shaped protrusion having a planar end section for creating hydrodynamic cavitation.

FIG. 6 is a perspective view of a rectangular-shaped protrusion for creating hydrodynamic cavitation.

FIG. 7 is a perspective view of a cylindrical-shaped protrusion for creating hydrodynamic cavitation.

FIG. 8 is a perspective view of a semi-circular-shaped protrusion for creating hydrodynamic cavitation.

FIG. 9 is a perspective view of a bullet-shaped protrusion for creating hydrodynamic cavitation.

DETAILED DESCRIPTION OF INVENTION

Figure 1:
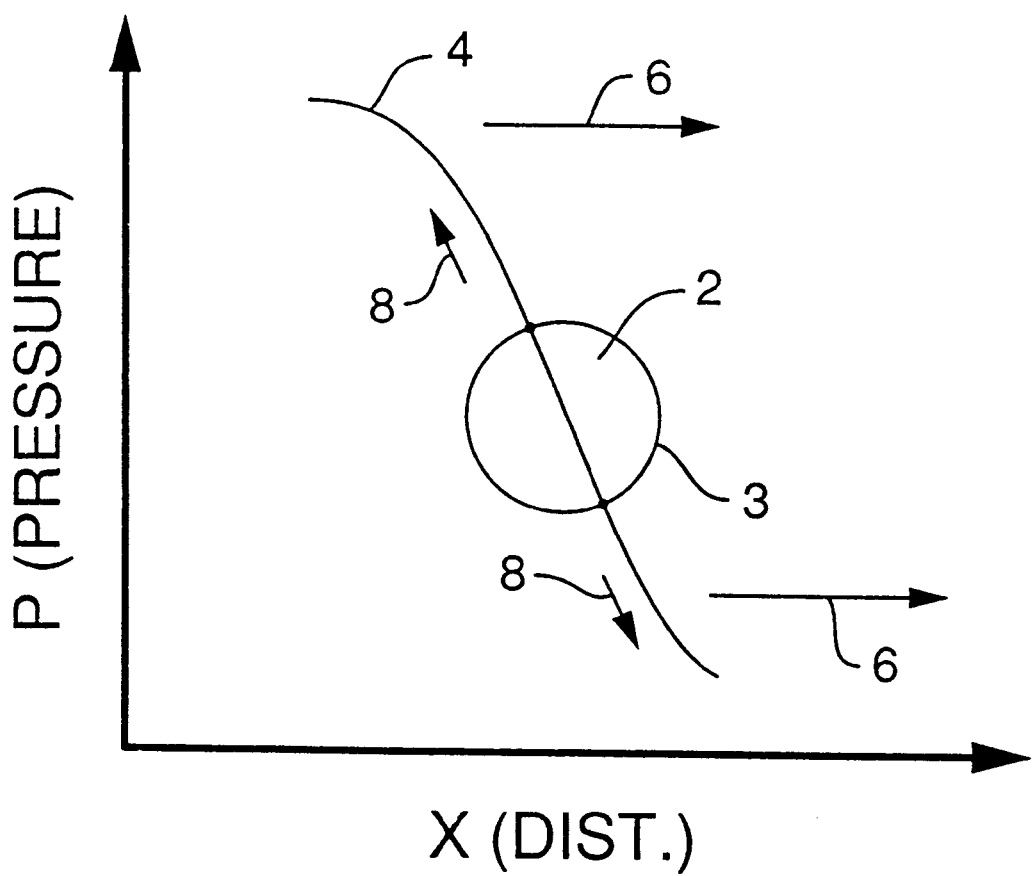
FIG. 1 is a cross-section view illustrating the stress effects of a shock wave on a bacteria wall.
Figure 2:
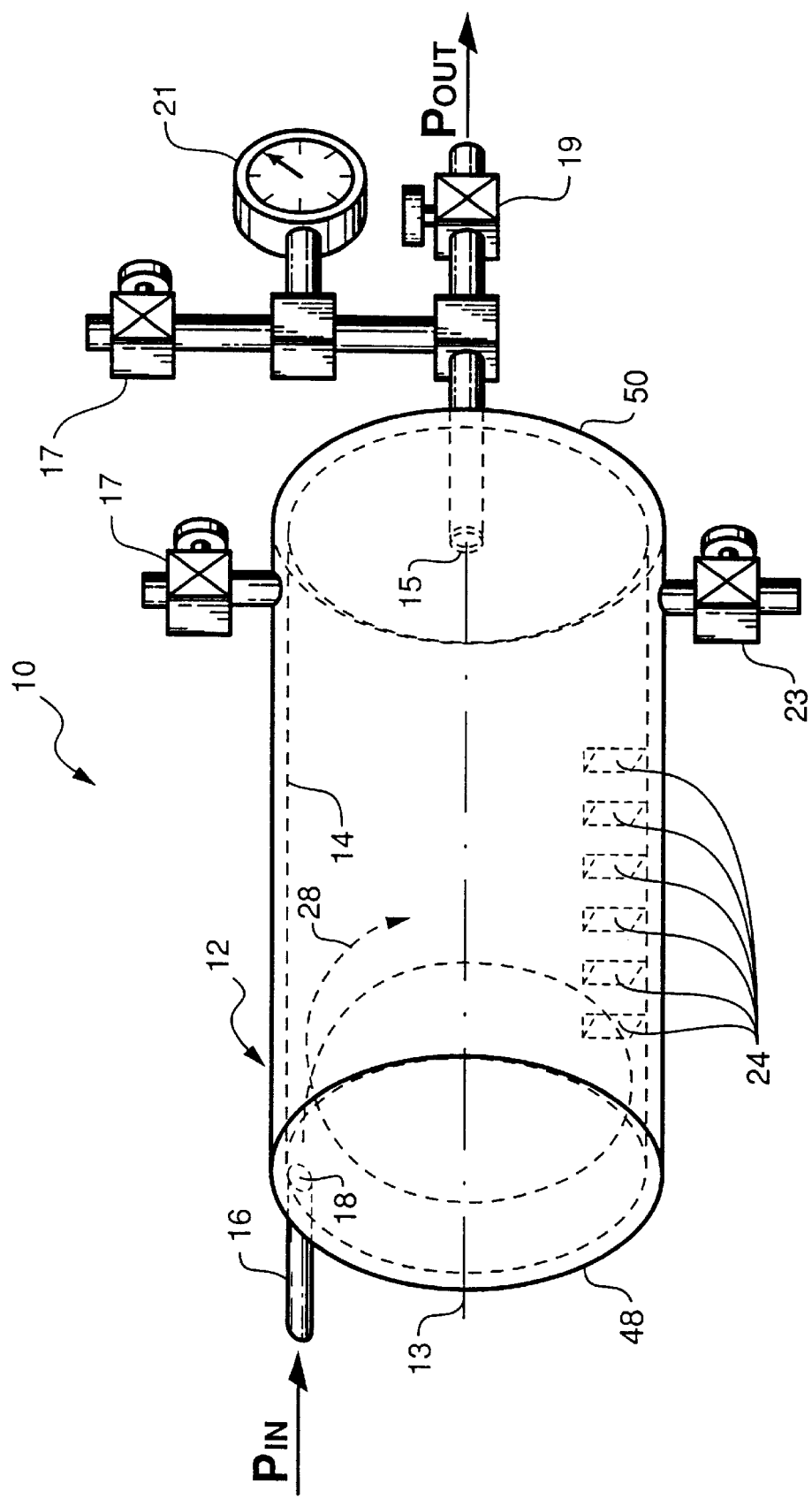
FIG. 2 is a perspective view of a liquid sterilizer incorporating teachings of the present invention.

FIG. 2 provides an overview of the salient operating features of a portion of the preferred embodiment of a liquid sterilization apparatus 10 embodying teachings of the present invention.

The apparatus 10 comprises a high pressure cylindrical chamber 12 with smooth inner walls 14 to reduce the hydrodynamic drag. The liquid is injected through the high pressure inlet nozzle 16. The inlet nozzle 16 is designed to provide maximum liquid velocity at the inlet nozzle outlet 18 at a minimum pressure loss. For a cylindrical nozzle, this condition translates into a 30–40 calibers long tube 20 (see FIG. 3). In hydrodynamic terms, the ratio of the length over the tube diameter equals the caliber. A 30–40 caliber long tube 20 provides the highest velocity for a given pressure drop, which is valid when the tube diameter size is significantly larger than the laminar boundary layer.

A preferred nozzle shape is a small angle cone 22 with the outlet cross-section smaller than the inlet (see FIG. 3). For low-viscosity liquids, such as water, the cross-section ratio is basically equal at the beginning and end of tube 20. For high viscosity liquids the cross-section ratio must be different at the inlet and outlet. The static pressure at the inlet nozzle outlet 18 is close to the static pressure in the chamber 12. Therefore, cavitation bubbles are not formed at the transition cross-section between the inlet nozzle outlet 18 and the chamber 12. The high velocity eddy flow 28 in the chamber 12 propagates along the chamber wall 14 and hits a series of super-cavitation blades 24 (see FIG. 2). The cross-section of the blades 24 is shown in FIG. 4, which incorporates the standard super-cavitating speedboat screw blades design with reduced drag. The blade angle 26 in this design is 14–30 degrees. One skilled in the art of creating a high-pressure drop in the flow behind an obstruction, and thereby creating high-pressure dynamic cavitation, will recognize that various other shapes of protrusions from the side wall will suffice, including but not limited to, a cylindrical-shaped post 40, a rectangular-shaped post 38, a semi-circular-shaped post 42, a bullet-shaped post 44, or a laminar flow body shape 34 with a planar end 36 (see FIGS. 5–9).

Figure 10:
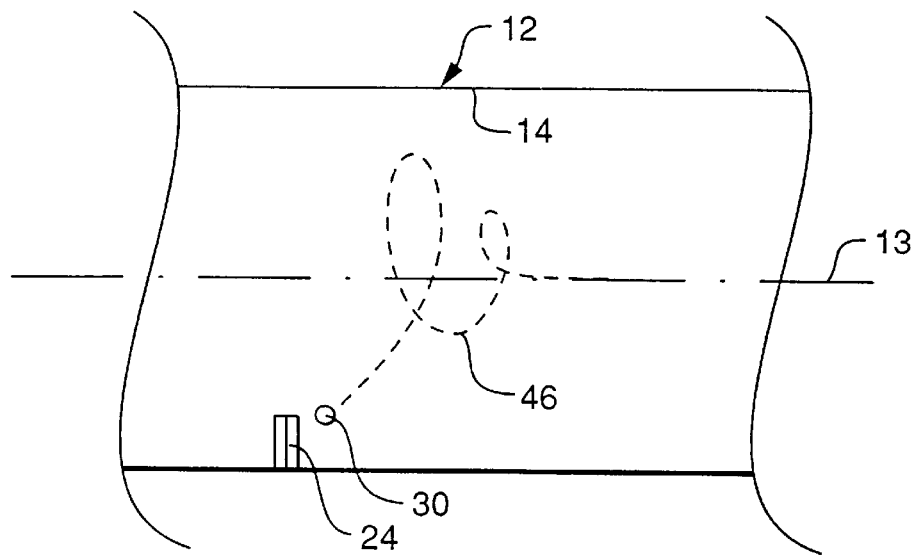
FIG. 10 is a cross-section view of the trajectory of a cavitation bubble inside the chamber of the device shown in FIG. 2.

The pressure drop behind the blade 24 creates cavitation bubbles 30 (see FIG. 4). The cavitation bubbles 30 have a typical life-time of 1–20 micro-seconds and are involved in a complex motion. They are dragged by the eddy flow 28 and they tend to buoy to the chamber axis 13 (see FIG. 2). Their buoyancy is much different from a gas bubbled in a glass of water. At a typical liquid flow velocity (v) of 20–30 meter/second and a chamber 12 radius (r) of a few centimeters, the acceleration $a=v^2/r$ corresponds to $10^4$–$10^6$ times the earth's gravity. This combined force results in a bubble trajectory 46 resembling a spiral, converging to the chamber axis 13, as illustrated in FIG. 10.

Figure 11:
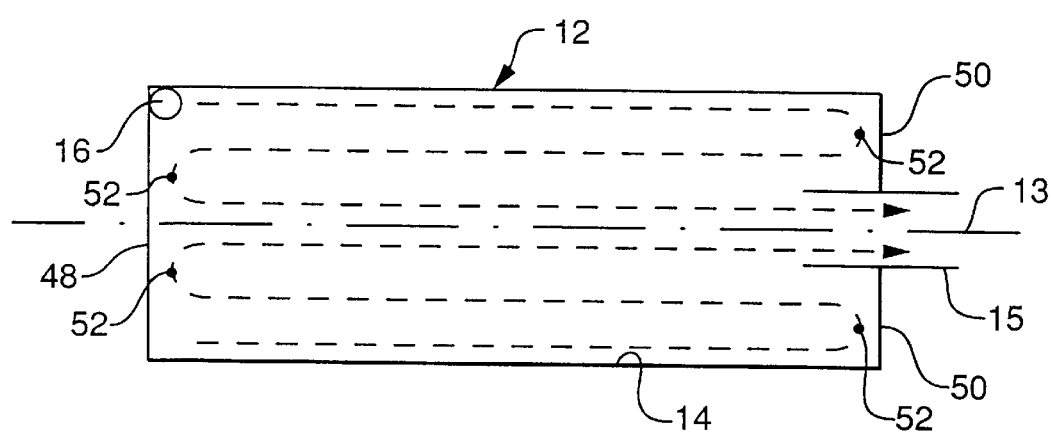
FIG. 11 is a cross-section view of the flow pattern of the liquid inside the chamber of the device shown in FIG. 2.

The bubble 30 can collapse at any point along its trajectory and create a shock wave. With a low drag on the flow and numerous blades 24, most of the chamber 12 volume constitutes a developed cavitation zone. The flow is organized in such a way that any given volume of liquid spends extra time near the chamber inner walls 14, where the bubbles are more numerous. This flow pattern is achieved by a special eddy outlet nozzle 15 (see FIGS. 2, 11) disposed on the second opposing end 50 of the chamber 12. This outlet nozzle 15, which is essentially a tube with an internal diameter much larger than that of an injection nozzle, is inserted along the chamber axis 13 to a distance, comparable with the chamber 12 radius. This creates a flow pattern as illustrated in FIG. 11, which depends on the inlet velocity, drag viscosity, pressure and the length/diameter ratio. Turning points 52 of the liquid flow occur at the first opposing end 48 and second opposing end 50 of the chamber 12. The location of the outlet nozzle 15 must be at the chamber axis 13. The diameter of the outlet nozzle is critical. Moreover, a pressure valve may be used to control the liquid flow from the outlet nozzle 15.

If the apparatus 10 is run in a fixed regime without a pressure regulating valve, the cross-section of the outlet nozzle 15 can be estimated from the Bernoulli equation and the pump flow rate. If the pump flow rate is signified by G ($m^3$/s), the liquid velocity at the outlet is v=G/S, where S is the cross-sectional area of the outlet nozzle 15. From the Bernoulli equation, the pressure before the outlet nozzle 15 follows the equation $P=\rho v^2$, where $\rho$ is the liquid density ($Kg/m^3$) and P is the required pressure. The resulting equation is $P=\rho(G/S)^2$, resulting in $S=(\rho G^2/P)^{1/2}$. For example, S would equal 8 $mm^2$, when G=250 ml/s and P=10 MPa. This estimation is true when the pump provides a high enough pressure to accelerate the liquid in the inlet nozzle 16 to a sufficiently high velocity, for example about 30 m/s, with an elevated pressure in the chamber 12 itself.

As illustrated in FIG. 11, the liquid flow from the inlet nozzle 16 is deflected by the second opposing end 50 and then again by the first opposing end 48 before exiting the chamber 12 out the outlet eddy nozzle 15. In theory, even thinner layers of eddy liquid motion are possible, resulting in more than two turning points 52.

In FIG. 2, the static pressure in the chamber 12 is regulated by a pressure regulating valve 19 and is measured by a manometer 21. The contaminated liquid is introduced through the inlet valves 17. At least two inlet valves 17 are needed, since one is for bleeding the air during fill-in. Purified liquid is released through the outlet valve 23. Inlet and outlet appendices are typically not ventilated by the liquid flow. However, since they have air pockets, the oscillating static pressure efficiently vents the liquid. Both passive (flexible hoses) and active (e.g., pressure regulating valve 19) pressure oscillation means can be used to vent appendices and to eliminate contaminated zones inside the apparatus 10.

Figure 12:
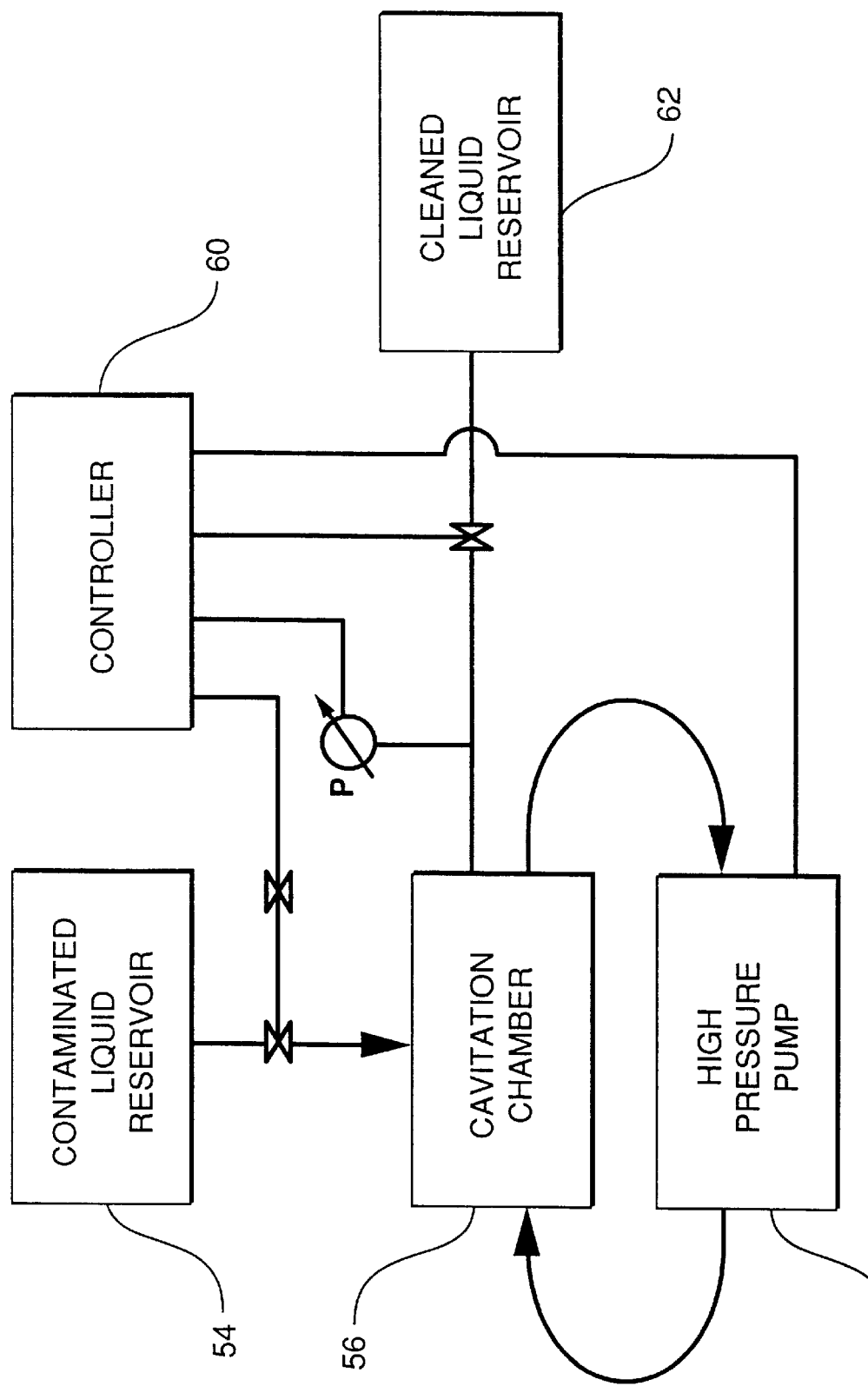
FIG. 12 is a block diagram of the present invention.

A block diagram of a liquid sterilization apparatus is shown in FIG. 12, where a high-pressure pump 58 circulates contaminated liquid introduced into a cavitation chamber 56 from a contaminated liquid reservoir 54. A controller 60 operates the process and the purified liquid is collected in a purified liquid reservoir 62.

EXAMPLE 1

A liquid sterilization apparatus 10, shown in FIG. 2, utilized a CW2040 car wash pump, which provided a maximum pressure of 2000 psi and a maximum flow rate of 4 gpm. The pump was driven by a Westinghouse 5 HP electric motor at 1100 RPM.

The cavitation chamber 12 comprised a SS-316 stainless steel tube with a length of 400 mm, an internal diameter of 50 mm, and a wall 14 thickness of 5 mm. Two 80×80 mm SS-316 plates with 6 mm thickness were welded on the first end 48 and second end 50 of the chamber 12. A thick wall SS-316 tube having an internal diameter of 2.5 mm (inlet nozzle 16) and a length of 80 mm was inserted tangentially to the chamber 12 internal surface and welded from the outside. A ¼" NPT connector was welded on the other end of the inlet nozzle 16. With this connector, the inlet nozzle 16 was connected with the pump outlet by ¼" flexible hose, rated at 3000 psi. The distance from the inlet nozzle 16 to the first end plate 48 was 10 mm. Six triangle slots were machined in the chamber walls 12 starting at 25 mm from the first end plate 48 with 20 mm spacing between the slots. The super-cavitating blades 24 comprised prisms precision machined of SS-316 with a sharp angle of 14 degrees, a height of 17 mm, a width of 3 mm, and a length of 9.7 mm. The blades 24 were inserted in the triangle slots and welded from the outside of the chamber 12. The outlet nozzle 15, having an internal diameter of 12 mm and a wall thickness of 2 mm, was inserted 20 mm along the chamber axis 13 and welded to the second end plate 50. The outlet nozzle 15 had a ⅜" fitting connected to a cross with a manometer 21 (2000 PSI), fill-in valve 17 and pressure regulating valve 19 (EVCO). The pressure regulating ball valve 19, through a flexible hose (⅜", rated 2000 PSI), was connected to the pump inlet. Fittings for another fill-in valve 17 and the outlet valve 23 were welded into the chamber 12 at a distance of 20 mm from the second end plate 50. SWAGELOK BVM4 SS-316 valves (10,000 PSI) were used.

The distance between the blades 24 is derived from the following considerations. The axial liquid flow velocity $V_a$ can be written as: $V_a=(Gn)/S$, where G is the pump flow rate (1/s), S is the chamber 12 cross-section, and n is the number of passes before exiting the chamber 12. Assuming that a cavitation bubble formed at the blade 24 is not buoyant and has an average life-time of $\tau_o$, the cavitation bubble during its life will move axially to a distance $x=V_a\tau_o=((Gn)/S)\tau_o$. In the present example with n=3, $\tau_o$=10–20 ms, and with a given chamber 12 size, the distance between the blades 24 corresponds to a 15–20 mm axial distance. A smaller chamber 12 radius or a higher pump flow rate will require greater spacing between the blades 24.

TEST RESULTS

Organisms

Cultures of *E. coli* (ATCC 25922) were maintained on agar plates in a refrigerator. Before the experiment was performed, an inoculum of the cell culture was transferred to 50 ml of sterile Tryptic Soy Broth (TSB) without Dextrose (DIFCO, Detroit, Mich.). The cells were grown in 250 ml sterilized Erlenmeyer glass containers for 16 hours at 37° C. under constant shaking (50 rpm), to facilitate the diffusion of air into the growth medium. Several 50 ml bacterial suspension samples were grown simultaneously and were later combined in a sterilized 500 ml beaker before the experiment. Sterilization of the glassware was performed in an autoclave at 121° C. for 15 min.

Assessing Bacterial Viability

Bacterial viability in suspensions was assessed by plating serial dilutions onto a nutrient agar and incubating the agar plates for 24 to 48 hours at 37° C. before counting. To perform serial dilutions, eight sterilized test tubes were each filled with 0.9 ml sterilized physiological saline solution (PSS); 100 µl of the initial suspension was transferred by a pipette into the first test tube using the sterilized pipette tip. The sample was vortexed and 100 µl of this sample was transferred onto the agar plate and spread around with a biological glass hockey stick. In order to calculate the final number of viable cells in 1 ml of the initial cell suspensions, the number of colonies grown on this agar plate is multiplied by $10^2$. This was due to the initial suspension being diluted ten-fold, and only 100 µl of the diluted suspension was seeded. Another 100 µl of this diluted sample was transferred into the next test tube containing 0.9 ml sterilized PSS, vortexed and plated to give $10^3$ dilution. This procedure (diluting and plating) was repeated until a $10^8$ dilution was achieved. Fresh sterile pipette tips were used in each case. Each plating was repeated in triplicate, and the average bacterial concentration was calculated.

Upon plating, the agar plates were turned with the agar side up and incubated at 37° C. for 36–48 hours. The number of colonies was counted to give a CFU value (Colony Forming Units in number CFU per ml).

Results

The initial concentration of bacteria in suspensions upon 16 hours of growth was $(6-8)\times 10^8$ CFU/ml.

In the first test, the initial bacterial suspension was diluted two-fold. The initial bacterial concentration in this sample was $CFU_O=(3-4)\times 10^8$ CFU/ml. One liter of this suspension was placed into the liquid sterilization apparatus 10. The suspension was allowed to circulate for 70 seconds without pressure, upon which the sample was taken and plated as described above. The measured CFU/ml in this sample $CFU_{70}$ was $5\times 10^8$, indicating no bacterial killing (slightly higher CFU than in the initial suspension may be due to breaking bacterial clusters during circulation through the apparatus).

The experiment continued for a total of 220 seconds, with a low pressure (up to 100 psi) given for several seconds. The concentration of bacteria measured in a final sample of this test was $CFU_{220}=1\times 10^8$, which is somewhat lower than in the initial suspension, indicating slight bacterial killing.

In the second test, initial bacterial suspension was diluted about 12 times before the experiment. In the control sample, $CFU_O=7\times 10^7$ CFU/ml. The experiment lasted for 178 seconds. The pressure was 200–500 psi for about 178 seconds. The $CFU_{178}=1\times 10^4$ indicated that about 4 orders of magnitude of bacterial killing occurred. Plating this suspension the following day revealed no viable bacteria.

The water temperature during the test remained below 40° C. The outlet appendix was flushed with water circulated in the device (~50 ml) to avoid pocket effects.

Figure 13:
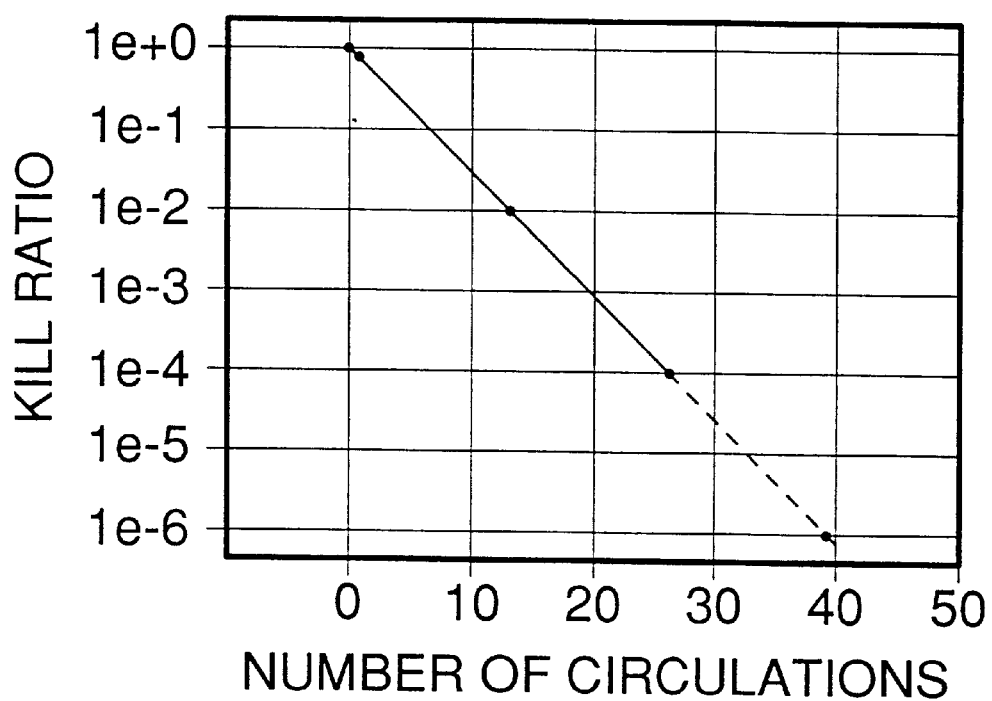
FIG. 13 is a graph showing the kill ratio of bacteria per the number of circulations for an experiment performed on the present invention.

The plot of the bacteria kill ratio is shown in FIG. 13. Recalculated values correspond to a 24% bacteria killing in one water circulation lasting about 6 seconds at 500 psi.

In summary, the method and apparatus disclosed herein is a significant improvement over the present state of the art of liquid flow sterilization.

The invention may be embodied in other specific forms without departing from its spirit or essential characteristics. Moreover, the present invention has applications for killing bacteria in other liquids, such as fossil fuels. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for sterilization of a continuous flow of liquid comprising:

a fluid passage through which the continuous flow of liquid passes, the fluid passage defined by a closed cylindrical chamber having a side wall and first and second opposing ends, the chamber having an inlet and an outlet through which the continuous flow of liquid enters and exits the chamber, the inlet being tangential to the chamber axis and adjacent to the first end to provide tangential flow within the chamber and to cause the liquid flow to be deflected at the first and second opposing ends two or more times for increasing sterilization time of the liquid before exiting the outlet axially disposed on the second end; and one or more projections partially protruding inside the chamber from the side wall for creating a high-pressure drop in the liquid flow behind the one or more projections and thereby creating high-pressure dynamic cavitation.

2. An apparatus according to claim 1, wherein said inlet comprises a high-pressure cylindrical nozzle having a tube length of about 30 to 40 calibers.

3. An apparatus according to claim 2, wherein the shape of said nozzle is a small angle cone.

4. An apparatus according to claim 3, wherein said cone has an outlet cross-section smaller than an inlet cross-section.

5. An apparatus according to claim 3, wherein said cone has an outlet cross-section equal to an inlet cross-section.

6. An apparatus according to claim 1, wherein said outlet is located on the cylindrical chamber axis.

7. An apparatus according to claim 1, wherein said outlet comprises an eddie nozzle.

8. An apparatus according to claim 1, wherein said one or more projections comprises one or more wedge-shaped cavitation blades having a pointed end facing the liquid flow.

9. An apparatus according to claim 1, wherein said one or more projections are laminar flow bodies shaped with a planar end section.

10. An apparatus according to claim 1, wherein said one or more projections comprises one or more rectangular posts.

11. An apparatus according to claim 1, wherein said one or more projections comprises one or more cylindrical posts.

12. An apparatus according to claim 1, wherein said one or more projections comprises one or more semi-circular posts.

13. An apparatus according to claim 1, wherein said one or more projections comprises one or more posts having a bullet-shaped end facing the liquid flow.

14. An apparatus according to claim 1, further comprising means for regulating static pressure in the chamber.

15. An apparatus according to claim 1, further comprising means for releasing contaminated zones within the chamber.

16. A method for sterilizing and purifying a continuous flow of liquid comprising the steps of:

pressurizing the liquid flow;

passing the liquid through a fluid passage, said fluid passage defined by:

a closed cylindrical chamber having a side wall and first and second opposing ends, the chamber having an inlet and an outlet through which the continuous flow of liquid enters and exits the chamber, the inlet being tangential to the chamber axis and adjacent to the first end to provide tangential flow within the chamber and to cause the liquid flow to be deflected at the first and second opposing ends two or more times for increasing sterilization time of the liquid before exiting the outlet axially disposed on the second end; and one or more projections partially protruding inside the chamber from the side wall for creating a high-pressure drop in the liquid flow behind the one or more projections and thereby creating high-pressure dynamic cavitation;

regulating static pressure in the chamber; and releasing the sterilized liquid from the chamber.

* * * * *